US010368806B2

(12) United States Patent
Kim

(10) Patent No.: US 10,368,806 B2
(45) Date of Patent: Aug. 6, 2019

(54) AUTONOMOUS SMART CAR CAPABLE OF FIRST AID AND METHOD FOR OPERATING THEREOF

(71) Applicants: HANCOM, INC., Seongnam-si, Gyeonggi-do (KR); Sang Cheol Kim, Namyangju-si, Gyeonggi-do (KR)

(72) Inventor: Sang Cheol Kim, Namyangju-si (KR)

(73) Assignees: HANCOM, INC., Seongnam-si, Gyeonggi-do (KR); Sang Cheol Kim, Namyangju-si, Gyeonggi-do (KR)

( * ) Notice: Subject to any disclaimer, the term of this patent is extended or adjusted under 35 U.S.C. 154(b) by 0 days.

(21) Appl. No.: 15/573,829

(22) PCT Filed: May 12, 2016

(86) PCT No.: PCT/KR2016/005041
§ 371 (c)(1),
(2) Date: Nov. 13, 2017

(87) PCT Pub. No.: WO2016/186380
PCT Pub. Date: Nov. 24, 2016

(65) Prior Publication Data
US 2018/0256420 A1    Sep. 13, 2018

(30) Foreign Application Priority Data

May 15, 2015    (KR) .......................... 10-2015-0068211

(51) Int. Cl.
*A61B 5/00*    (2006.01)
*B60Q 1/46*    (2006.01)
(Continued)

(52) U.S. Cl.
CPC .......... *A61B 5/6893* (2013.01); *A61B 5/0022* (2013.01); *A61B 5/02055* (2013.01);
(Continued)

(58) Field of Classification Search
CPC ... A61B 5/6893; A61B 5/02055; A61B 5/747; A61B 5/7282; A61B 5/0022;
(Continued)

(56) References Cited

U.S. PATENT DOCUMENTS 6,889,137 B1 *    5/2005    Rychlak ............. G01C 21/3407
340/286.07
6,944,536 B2 *    9/2005    Singleton ............... G01C 21/20
340/995.19
(Continued)

FOREIGN PATENT DOCUMENTS

KR    20-0307666 Y1    3/2003
KR    10-0800026 B1    2/2008
(Continued)

OTHER PUBLICATIONS

International Search Report for PCT/KR2016/005041 dated Aug. 12, 2016 from Korean Intellectual Property Office.

*Primary Examiner* — Peter D Nolan
(74) *Attorney, Agent, or Firm* — Revolution IP, PLLC

(57) ABSTRACT

An autonomous smart car includes a bio-signal sensing unit sensing a bio-condition of a person in the autonomous smart car; a communication unit supporting wireless communication between the autonomous smart car and an external of the autonomous smart car; a memory unit storing basic data of the person in the autonomous smart car, general bio-signal data, bio-signal data sensed by the bio-signal sensing unit, and hospital information data; an autonomous driving unit autonomously driving the autonomous smart car to a destination; an emergency handling unit enabling the autonomous smart car to inform that an emergency patient is in the autonomous smart car to outside when the bio-condition of the person in the autonomous smart car indicates an emergency; and a control unit analyzing a current condition of the (Continued)

person by comparing a bio-signal sensed by the bio-signal sensing unit with the data stored in the memory unit.

9 Claims, 2 Drawing Sheets

(51) Int. Cl.
*A61B 5/0205* (2006.01)
*B60Q 1/26* (2006.01)
*B60Q 1/50* (2006.01)
*G08G 1/0968* (2006.01)
*G01C 21/34* (2006.01)
*B60W 40/08* (2012.01)
*A61G 3/00* (2006.01)
*H04W 4/90* (2018.01)
*H04W 4/44* (2018.01)

(52) U.S. Cl.
CPC ............ *A61B 5/7282* (2013.01); *A61B 5/747* (2013.01); *B60Q 1/2611* (2013.01); *B60Q 1/46* (2013.01); *B60Q 1/50* (2013.01); *A61G 3/001* (2013.01); *B60W 2040/0872* (2013.01); *G01C 21/3407* (2013.01); *G05D 2201/0212* (2013.01); *G08G 1/096838* (2013.01); *H04W 4/44* (2018.02); *H04W 4/90* (2018.02)

(58) Field of Classification Search
CPC .......... B60Q 1/2611; B60Q 1/50; B60Q 1/46; G01C 21/3407; G08G 1/096838; B60W 2040/0872; H04W 4/90; H04W 4/44; A61G 3/001; G05D 2201/0212
See application file for complete search history.

(56) References Cited

U.S. PATENT DOCUMENTS

| | | | | |
|---|---|---|---|---|
| 7,877,275 | B2* | 1/2011 | Ball | A61B 5/411 705/3 |
| 8,874,301 | B1* | 10/2014 | Rao | B60K 28/066 180/272 |
| 9,144,389 | B2* | 9/2015 | Srinivasan | A61B 5/0408 |
| 9,157,752 | B1* | 10/2015 | Fernandez Garcia | G01C 21/34 |
| 10,007,263 | B1* | 6/2018 | Fields | G06F 8/65 |
| 2004/0204837 | A1* | 10/2004 | Singleton | G01C 21/20 701/410 |
| 2005/0107673 | A1* | 5/2005 | Ball | A61B 5/411 600/301 |
| 2007/0265540 | A1* | 11/2007 | Fuwamoto | A61B 5/04525 600/515 |
| 2009/0198733 | A1* | 8/2009 | Gounares | G06F 19/3418 |
| 2011/0117878 | A1* | 5/2011 | Barash | H04W 4/90 455/404.2 |
| 2012/0059227 | A1* | 3/2012 | Friedlander | A61B 5/0022 600/300 |
| 2012/0256769 | A1* | 10/2012 | Satpathy | G08B 13/19647 340/989 |
| 2014/0104405 | A1* | 4/2014 | Weidl | A61B 5/02416 348/77 |
| 2014/0135598 | A1* | 5/2014 | Weidl | A61B 5/0205 600/301 |
| 2014/0221781 | A1* | 8/2014 | Schrauf | A61B 5/0205 600/301 |
| 2014/0277894 | A1 | 9/2014 | Doyle et al. | |
| 2015/0066284 | A1* | 3/2015 | Yopp | B60W 30/00 701/29.2 |
| 2015/0105687 | A1* | 4/2015 | Abreu | A61B 5/01 600/549 |
| 2015/0233719 | A1* | 8/2015 | Cudak | B60R 25/01 701/23 |
| 2015/0276415 | A1* | 10/2015 | Shrinath | G01C 21/36 701/1 |
| 2015/0338227 | A1* | 11/2015 | Kruecken | G01C 21/3697 701/410 |
| 2016/0071418 | A1* | 3/2016 | Oshida | G08G 1/22 701/23 |
| 2016/0151021 | A1* | 6/2016 | Feng | A61B 5/6893 600/484 |

FOREIGN PATENT DOCUMENTS

| | | |
|---|---|---|
| KR | 10-1091274 B1 | 12/2011 |
| KR | 10-2014-0129710 A | 11/2014 |
| WO | 2014/150626 A1 | 9/2014 |

* cited by examiner

AUTONOMOUS SMART CAR CAPABLE OF FIRST AID AND METHOD FOR OPERATING THEREOF

CROSS REFERENCE TO PRIOR APPLICATIONS

This application is a National Stage Application of PCT International Patent Application No. PCT/KR2016/005041 filed on May 12, 2016, under 35 U.S.C. § 371, which claims priority to Korean Patent Application No. 10-2015-0068211 filed on May 15, 2015, which are all hereby incorporated by reference in their entirety.

TECHNICAL FIELD

The present invention relates to autonomous smart cars. More particularly, the present invention relates to an autonomous smart car capable of first aid and method of operating the same that can sense a bio-signal of a person in an autonomous smart car for autonomous transport to hospital.

BACKGROUND ART

Recently, as image processing-related technologies and performances of sensors and hardware, etc. have rapidly developed, research on unmanned cars is competitively proceeding.

Actually, a GPS navigation device has already been popularized as a navigation service for drivers. Also, accuracy of GPS data has been gradually improved, and reliability has increased due to small error range.

The newest unmanned cars autonomously drive and park by utilizing a camera for observing forward and backward, a front-side radar sensor, the GPS, etc.

Since unmanned cars are an inevitable trend, research thereon has been conducted in various directions, but until now, they have been studied mainly only on unmanned driving of cars.

DISCLOSURE

Technical Problem

Accordingly, the present invention has been made keeping in mind the above problems occurring in the related art, and an object of the present invention is to provide an autonomous smart car capable of first aid and a method of operating the same, the autonomous smart car being provided with a sensing unit sensing a bio-signal of a person in the autonomous smart car that can autonomously drive, whereby when an emergency or a situation needed to go to hospital occurs an emergency person can be autonomously transported to an appropriate hospital based on sensed data.

Technical Solution

In order to accomplish the above object, the present invention provides an autonomous smart car capable of first aid, the autonomous smart car including: a bio-signal sensing unit sensing a bio-condition of a person in the autonomous smart car that autonomously drives; a communication unit supporting wireless communication between the autonomous smart car and an external of the autonomous smart car; a memory unit storing basic data of the person in the autonomous smart car, general bio-signal data, bio-signal data sensed by the bio-signal sensing unit, and hospital information data; an autonomous driving unit autonomously driving the autonomous smart car to a destination; an emergency handling unit enabling the autonomous smart car to inform that an emergency patient is in the autonomous smart car to outside when the bio-condition of the person in the autonomous smart car indicates an emergency; and a control unit analyzing a current condition of the person by comparing a bio-signal sensed by the bio-signal sensing unit with the data stored in the memory unit, the control unit searching for a hospital where the autonomous smart car can arrive from a current location and controlling the autonomous smart car through the memory unit and the autonomous driving unit to autonomously drive to the hospital when determined as an emergency.

Here, the basic data of the person in the autonomous smart car may be data on at least one of a name, an age, a phone number, known diseases, treatment history, and a hospital where the person usually goes, the general bio-signal data may include emergency data and normal range data on a body temperature, a heartbeat, and a pulse, and the hospital information data may be at least one of emergency room information of a hospital, specialty information of a hospital and location information thereof, phone number information, and communication path information to each hospital server.

The hospital information data may be updated at a preset period through the communication unit.

Also, the autonomous driving unit may include: a location information receiver receiving information on a current location of the car; a traffic information receiver receiving traffic information to a destination when driving the autonomous smart car; and an autonomous driving controller enabling the autonomous smart car to autonomously drive from the current location of the car received by the location information receiver to the destination.

In the meantime, the emergency handling unit may include: a warning light part informing that the emergency patient is in the autonomous smart car when an emergency occurs; a speaker part informing arrival of the emergency patient at a hospital; and an automatic call part automatically making a call to a destination hospital when the person in the autonomous smart car is an emergency patient as a sensing result of the bio-signal sensing unit, the automatic call part automatically transmitting the sensing result sensed by the bio-signal sensing unit with at least one of a gender, a name, a car number of the emergency patient, and information on a current location of the car.

Here, the control unit may control the warning light part to turn on a warning light and controls the automatic call part to make an automatic call to the destination hospital, or when the memory unit stores communication path information to a destination hospital server, the control unit may control the communication unit to transmit data that informs a condition of a patient to the destination hospital server.

In the meantime, the autonomous smart car may communicate through a wired/wireless communication network with a hospital information provision server providing at least one piece of hospital information on a location, a specialty, and working hours of a hospital and a traffic information provision server providing traffic information in real-time.

Also, in order to accomplish the above object, the present invention provides a method of operating an autonomous smart car capable of first aid, the method including: sensing, by a bio-signal sensing unit of an autonomous smart car, a bio-signal of a person in the autonomous smart car; analyzing, by a control unit of the autonomous smart car, the bio-signal sensed by the bio-signal sensing unit; searching, by the control unit of the autonomous smart car, for a hospital to which an emergency patient is transported through a memory unit storing hospital information when determining the sensed bio-signal indicates an emergency; and controlling, by the control unit of the autonomous smart car, an autonomous driving unit to autonomously drive the autonomous smart car to a destination hospital.

At the analyzing, by the control unit of the autonomous smart car, of the bio-signal sensed by the bio-signal sensing unit, sensed data of the person in the autonomous smart car may be analyzed by being compared with emergency data and normal range data on a body temperature, a heartbeat, and a pulse.

In the meantime, the searching for the hospital to which the emergency patient is transported may further include communicating with a hospital information provision server providing hospital information through a communication unit supporting wireless communication between the autonomous smart car and an external of the autonomous smart car.

Here, the controlling of the autonomous smart car to autonomously drive to the destination hospital may further include: making an automatic call to the hospital and transmitting at least one of a condition, a gender, a name, a car number of the emergency patient, and information on a current location of the car in a voice through an emergency handling unit informing that the autonomous smart car is in an emergency to outside; or transmitting data that informs the condition of the patient to a destination hospital server through the communication unit when there is communication path information to the destination hospital server.

The controlling of the autonomous smart car to autonomously drive to the destination hospital may further include: turning on a warning light part attached on the autonomous smart car, the warning light part informing that the autonomous smart car is in an emergency; outputting arrival of the patient in a voice through a speaker part outputting a voice when arrival at the destination hospital is confirmed; and turning off the warning light part and output of the speaker part when the emergency is ended.

Advantageous Effects

According to the present invention, the following effects may be obtained.

First, a sensing unit senses a bio-signal of a person in the autonomous smart car that can autonomously drive, whereby when an emergency or a situation needed to go to hospital occurs, an emergency person can be autonomously transported to an appropriate hospital based on sensed data.

Second, when a patient is unable to make a call, the autonomous smart car automatically calls a hospital and informs a condition of the patient, whereby it is possible to quickly cope with emergency.

Third, when transmitting a sensing result of a bio-signal through communication with a hospital server, it is possible to quickly cope with emergency such that a patient can be easily rescued from crises, compared to arrival of a patient at hospital.

BEST MODE

Exemplary embodiments of the present invention will be described in detail with reference to the accompanying drawings.

Also, all terms used herein should be construed as having meanings that are obvious to one of ordinary skill in the art. However, some terms may be arbitrarily selected by the applicant, and in this case, the meaning of the selected terms will be described in detail in the detailed description of the present invention. Thus, the terms used herein should be defined based on the meaning of the terms together with the description throughout the specification. Also, detailed description of well-known functions and structures incorporated herein may be omitted to avoid obscuring the subject matter of the present invention. This aims to omit unnecessary description so as to make the subject matter of the present invention clear.

Figure 1:
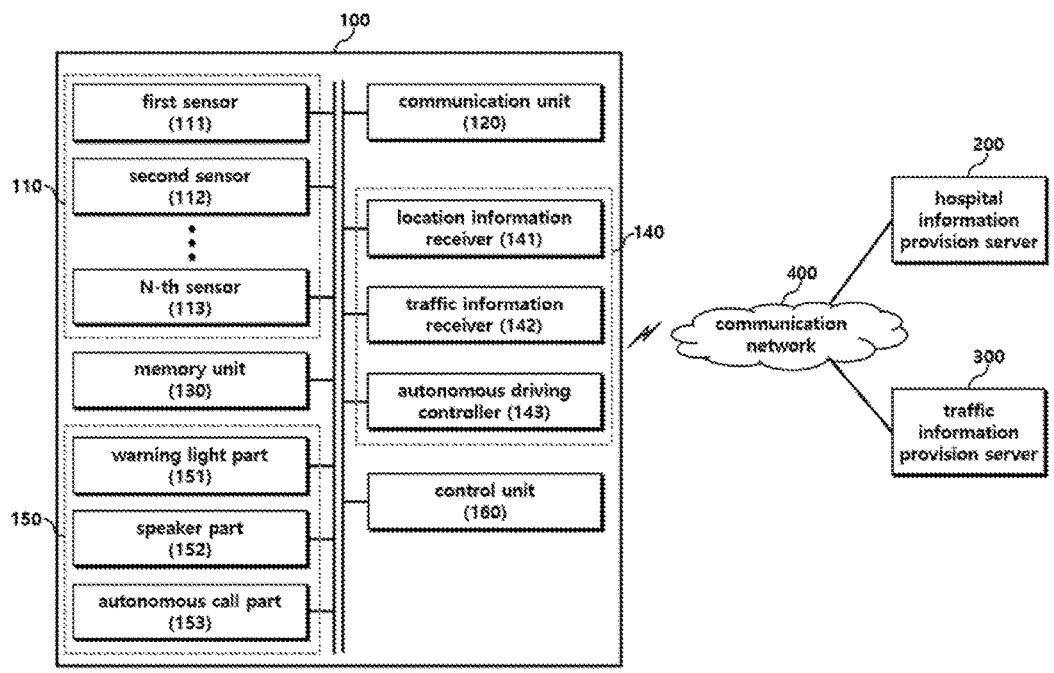
FIG. 1 is a block diagram illustrating an autonomous smart car capable of first aid according to the present invention.

FIG. 1 is a block diagram illustrating an autonomous smart car capable of first aid according to the present invention.

An autonomous smart car capable of first aid according to the present invention includes: a bio-signal sensing unit 110, a communication unit 120, a memory unit 130, an autonomous driving unit 140, an emergency handling unit 150, and a control unit 160 as shown in FIG. 1.

Here, the bio-signal sensing unit 110 is composed of the first to N-th sensors 111, 112, and 113 sensing electrical signals between microscopic cells of the human body. The sensors measure small signals ranging from uV to mV. For example, a condition of a person in a car is sensed by sensing an electromyogram, an electrocardiogram, etc.

The communication unit 120 of an autonomous smart car 100 communicates with a hospital information provision server 200 and a traffic information provision server 300 outside of the autonomous smart car.

The memory unit 130 stores basic data of a person in a car (a name, an age, a phone number, a medical history (known diseases, treatment history, a hospital where the person usually goes, etc.), general bio-signal data, sensed bio-signal data, and hospital information data. Here, the general bio-signal data includes normal range data on a body temperature, a heartbeat, a pulse, etc. and emergency data that are stored in tabular form. Also, the hospital information data includes emergency room information of a hospital, specialty information of a hospital, location information of a hospital, phone number information of a hospital, communication path information to each hospital server, etc. It is desired that the hospital information data is periodically updated through the communication unit 120.

The autonomous driving unit 140 includes a location information receiver 141, a traffic information receiver 142, and an autonomous driving controller 143.

Here, the location information receiver 141 receives information on a current location of a car.

The traffic information receiver 142 receives traffic information to a destination when driving the autonomous smart car 100.

The autonomous driving controller 143 enables the autonomous smart car 100 to autonomously drive from the current location received by the location information receiver 141 to a destination, and controls a steering system, a brake, an accelerator, and a transmission of the car.

The emergency handling unit 150 includes a warning light part 151, a speaker part 152, and an automatic call part 153. Here, the warning light part 151 informs that an emergency patient is in the car when an emergency occurs. The speaker part 152 informs arrival of the emergency patient at hospital. To this end, the speaker part 152 may be attached on outside of the car. In the meantime, based on a sensing result of the bio-signal sensing unit 110, it is determined that the person in the autonomous smart car 100 is an emergency patient and is unable to make a call (unconscious, etc.), the automatic call part 153 makes an automatic call to the destination hospital so as to automatically transmit a condition of a patient, gender of the patient, the name, the car number, and the information on the current location of the car.

The control unit 160 compares the bio-signal sensed by the bio-signal sensing unit 110 with data stored in the memory unit 130 to analyze a current condition of the sensed person. When determined as an emergency, a current location of the autonomous smart car 100 is detected by the location information receiver 141 and the optimum hospital appropriate for the current condition is searched through communication with the traffic information receiver 142 and the memory unit 130 or the hospital information provision server 200. Next, based on the search result, the autonomous smart car autonomously drives to a destination hospital through the autonomous driving controller 143.

Here, the control unit 160 turns on a warning light through the warning light part 151, and enables the automatic call part 153 to autonomously call the destination hospital. Alternatively, when the memory unit 130 stores communication path information to a destination hospital server, the control unit 160 controls the communication unit 120 to transmit data that informs the destination hospital server of a condition of a patient. Here, the autonomous smart car 100, the hospital information provision server 200, and the traffic information provision server 300 may communicate with each other through a wired/wireless communication network 400.

Figure 2:
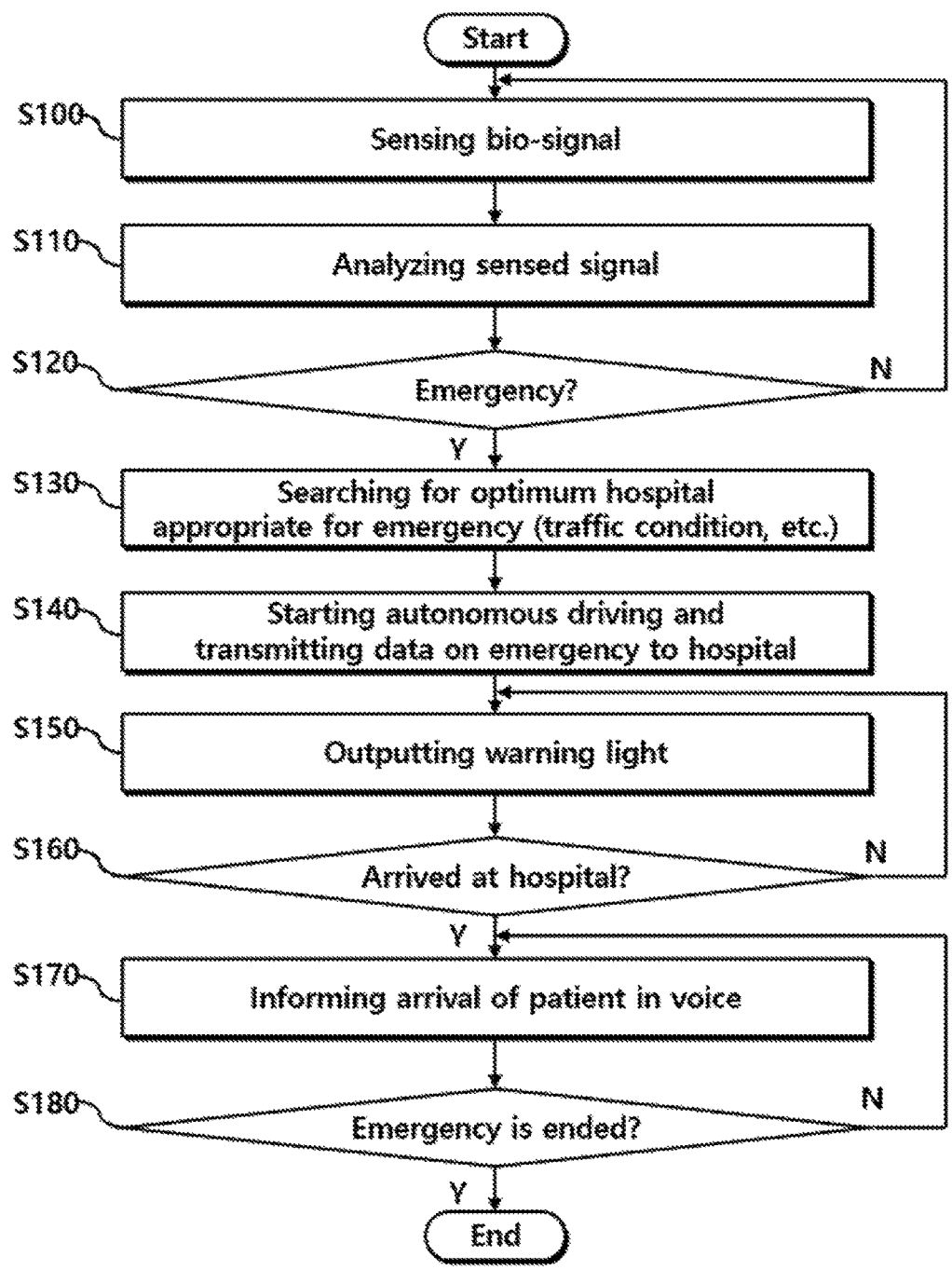
FIG. 2 is a flowchart illustrating a method of operating an autonomous smart car capable of first aid according to the present invention.

FIG. 2 is a flowchart illustrating a method of operating an autonomous smart car capable of first aid according to the present invention.

In the method of operating an autonomous smart car capable of first aid according to the present invention, as shown in FIG. 2, the bio-signal sensing unit 110 of the autonomous smart car 100 capable of first aid senses a bio-signal at step S100.

Next, the control unit 160 of the autonomous smart car 100 analyzes the sensed signal at step S110.

When determined as an emergency at step S120, the control unit 160 of the autonomous smart car 100 searches for the optimum hospital appropriate for the emergency through the memory unit 130 or the hospital information provision server 200 at step S130.

Next, the control unit 160 of the autonomous smart car 100 controls the autonomous driving unit 140 to autonomously drive to the destination hospital, and controls the emergency handling unit 150 to make an automatic call to a hospital so as to inform of a condition of a patient, gender of the patient, the name, the car number, and the information on the current location of the car related to emergency in a voice. Also, when the memory unit 130 stores communication path information to the destination hospital server, the control unit 160 of the autonomous smart car 100 controls the communication unit 120 to transmit data that informs a condition of a patient to the destination hospital server at step 140.

Also, the control unit 160 of the autonomous smart car 100 turns on the warning light part 151 of the emergency handling unit 150 at step 150.

In the meantime, the control unit 160 of the autonomous smart car 100 determines whether arrival at the destination hospital has occurred based on the reception result of the location information receiver 141 at step S160. When arrival at the destination hospital is confirmed, arrival of the patient is output (informed) in a voice through the speaker part 152 at step S170.

Next, whether an emergency has ended is determined at step S180. When the emergency is ended, the warning light and the voice output are turned off at step S180.

Although the present invention has been described with reference to the accompanying drawings, this is merely an example of various embodiments containing the subject matter of the present invention, and is intended to allow those skilled in the art to easily implement the present invention. Thus, it is clear that the present invention is not restricted to the embodiments described above. Therefore, the scope of the present invention should be construed by claims below, and all technical spirits that fall within an equivalent range by change, substitution, replacement, etc. within the subject matter of the present invention will be included in the scope of a right of the present invention. In addition, some components of the drawings are intended to more clearly describe configurations, and thus it is clarified that the components are exaggerated or minimized when compared to actual components.

INDUSTRIAL APPLICABILITY

The present invention senses a bio-signal of a driver in an autonomous smart car to autonomously drive to a hospital based on a result thereof, and can be used in a technology of handling an emergency by using an autonomous smart car.

The invention claimed is:

1. An autonomous smart car capable of first aid, comprising:
   a bio-signal sensing unit configured to sense that a person in the autonomous smart car is in need of the first aid;
   a communication unit configured to have a wireless communication with a hospital information provision server and a traffic information provision server;
   a memory unit storing basic data of the person in the autonomous smart car, general bio-signal data, bio-signal data sensed by the bio-signal sensing unit, and hospital information data,
      wherein the basic data includes a name, a medical treatment history of the person, and a hospital in which the person generally visits for a medical treatment,
      wherein the general bio-signal data includes emergency data and normal range data on a body temperature, a heartbeat, and a pulse, and
      wherein the hospital information data is at least one of emergency room information, specialty information and location information, phone number information, and communication path information to each hospital server;
   an autonomous driving unit configured to drive the autonomous smart car to a hospital autonomously, the autonomous driving unit comprising;
   a location information receiver configured to receive information of a current location of the autonomous smart car;

a traffic information receiver configured to receive traffic information to the hospital; and an autonomous driving controller enabling the autonomous smart car to autonomously drive from the current location of the car received by the location information receiver to the destination; and an emergency handling unit enabling the autonomous smart car to inform the hospital of the person in the autonomous smart car who is in need of the first aid; and a control unit configured to determine that the person is in need of the first aid by comparing a bio-signal sensed by the bio-signal sensing unit with the data stored in the memory unit, the control unit configured to select the hospital by:

detecting the current location via the location information receiver;

searching the hospital based on the medical treatment history of the person and the hospital in which the person generally visits for the medical treatment; and receiving the traffic information to the hospital via the traffic information receiver.

2. The autonomous smart car of claim 1, wherein the hospital information data is updated at a preset period through the communication unit.

3. The autonomous smart car of claim 1, wherein the emergency handling unit includes:

a warning light part informing that the person in need of the first aid is in the autonomous smart car when an emergency occurs;

a speaker part informing arrival of the person in need of the first aid at the hospital; and an automatic call part automatically making a call to the hospital when the person in the autonomous smart car is in need of the first aid as a sensing result of the bio-signal sensing unit, the automatic call part automatically transmitting the sensing result sensed by the bio-signal sensing unit with at least one of a gender, the name, a car number, and information on the current location of the car.

4. The autonomous smart car of claim 3, wherein the control unit controls the warning light part to turn on a warning light and controls the automatic call part to make an automatic call to the hospital, or when the memory unit stores communication path information to the hospital information provision server, the control unit controls the communication unit to transmit data that informs a condition of the person to the hospital information provision server.

5. The autonomous smart car of claim 1, wherein the autonomous smart car communicates through a wired and/or wireless communication network with the hospital information provision server providing at least one piece of hospital information on a location, a specialty, and working hours of the hospital and the traffic information provision server providing traffic information in real-time.

6. A method of operating an autonomous smart car capable of first aid, the method comprising:

sensing, by a bio-signal sensing unit of an autonomous smart car, that a person in the autonomous smart car is in need of the first aid;

analyzing, by a control unit of the autonomous smart car, the bio-signal sensed by the bio-signal sensing unit;

searching, by the control unit of the autonomous smart car, for a hospital to which the person in need of the first aid is transported through a memory unit storing hospital information when determining the sensed bio-signal indicates an emergency, wherein the memory unit includes a medical treatment history of the person, and a hospital in which the person generally visits for a medical treatment;

controlling, by the control unit of the autonomous smart car, an autonomous driving unit to autonomously drive the autonomous smart car to the hospital, wherein the autonomous driving unit includes a location information receiver configured to receive information of a current location of the autonomous smart car and a traffic information receiver configured to receive traffic information to the hospital;

detecting the current location via the location information receiver;

selecting the hospital based on the medical treatment history of the person and the hospital in which the person generally visits for the medical treatment; and receiving the traffic information to the hospital via the traffic information receiver, wherein at the analyzing, by the control unit of the autonomous smart car, of the bio-signal sensed by the bio-signal sensing unit, sensed data of the person in the autonomous smart car is analyzed by being compared with emergency data and normal range data on a body temperature, a heartbeat, and a pulse.

7. The method of claim 6, wherein the searching step further includes communicating with a hospital information provision server providing hospital information through a communication unit.

8. The method of claim 7, wherein the controlling step further includes:

making an automatic call to the hospital and transmitting at least one of a condition, a gender, a name, a car number of the person, and information on the current location of the car in a voice through an emergency handling unit informing that the autonomous smart car is in an emergency to outside; or transmitting data that informs the hospital server of the person in need of the first aid to through the communication unit when there is communication path information to the hospital information provision server.

9. The method of claim 7, wherein the controlling step further includes:

turning on a warning light part attached on the autonomous smart car, the warning light part informing that the autonomous smart car is in an emergency;

outputting arrival of the person in a voice through a speaker part outputting a voice when arrival at the hospital is confirmed; and turning off the warning light part and output of the speaker part when the emergency is ended.

* * * * *